United States Patent
Lorraine et al.

(10) Patent No.: US 10,076,267 B2
(45) Date of Patent: Sep. 18, 2018

(54) METHODS AND SYSTEMS FOR IMPROVED NAVIGATION

(71) Applicant: General Electric Company, Schenectady, NY (US)

(72) Inventors: Peter William Lorraine, Niskayuna, NY (US); Floribertus P. M. Heukensfeldt Jansen, Ballston Lake, NY (US)

(73) Assignee: General Electric Company, Schenectady, NY (US)

(*) Notice: Subject to any disclaimer, the term of this patent is extended or adjusted under 35 U.S.C. 154(b) by 956 days.

(21) Appl. No.: 14/505,893

(22) Filed: Oct. 3, 2014

(65) Prior Publication Data

US 2016/0095536 A1  Apr. 7, 2016

(51) Int. Cl.
| | | |
|---|---|---|
| H03F 1/26 | (2006.01) | |
| A61B 5/06 | (2006.01) | |
| G01R 33/09 | (2006.01) | |
| G01R 33/07 | (2006.01) | |
| A61B 5/00 | (2006.01) | |
| G01R 33/00 | (2006.01) | |
| G06F 11/30 | (2006.01) | |
| A61M 25/01 | (2006.01) | |

(52) U.S. Cl.
CPC ............ *A61B 5/062* (2013.01); *A61B 5/7203* (2013.01); *G01R 33/0029* (2013.01); *G01R 33/07* (2013.01); *G01R 33/072* (2013.01); *G01R 33/09* (2013.01); *G01R 33/091* (2013.01); *A61M 25/0127* (2013.01)

(58) Field of Classification Search
CPC .................................................... A61B 5/062
See application file for complete search history.

(56) References Cited

U.S. PATENT DOCUMENTS

| | | |
|---|---|---|
| 6,657,476 B1 | 12/2003 | Bicking |
| 6,927,570 B2 | 8/2005 | Simmonds et al. |
| 7,047,059 B2 | 5/2006 | Avrin et al. |
| 7,808,749 B2 | 10/2010 | Kou |
| 8,283,921 B2 | 10/2012 | Huber et al. |

(Continued)

FOREIGN PATENT DOCUMENTS

CN 2704174 Y 6/2005

*Primary Examiner* — Phuong Huynh
(74) *Attorney, Agent, or Firm* — GE Global Patent Operation; Pabitra K. Chakrabarti

(57) ABSTRACT

Systems and methods for navigation are presented. First and second response signals received from at least one magnetic sensor operatively coupled to a target device in response to a magnetic field are measured at reference and reversed sensitivity while an alignment of magnetic domains corresponding to the magnetic sensor remains unchanged. A useful portion of the first response signal is determined by eliminating common-mode noise from the first response signal based on a difference between the first and second response signals. Alternatively, a bias signal having a desired bias frequency is applied to shift a signal frequency of a response signal of a magnetoresistance sensor that includes common-mode noise. A useful portion of the response signal is determined by measuring the response signal at a shifted frequency that is a sum of the signal and bias frequencies. A position of the subject is then determined based on the useful portion.

9 Claims, 6 Drawing Sheets

(56) References Cited

U.S. PATENT DOCUMENTS

| | | | |
|---|---|---|---|
| 8,358,128 B2 | 1/2013 | Jensen et al. | |
| 8,483,800 B2 | 7/2013 | Jensen et al. | |
| 8,618,795 B1 | 12/2013 | Nagarkar et al. | |
| 9,002,437 B2 | 4/2015 | Yaroshenko et al. | |
| 9,351,800 B2 | 5/2016 | Groszmann et al. | |
| 2010/0113919 A1 | 5/2010 | Maschke | |
| 2010/0127696 A1* | 5/2010 | Huber | B82Y 25/00 324/207.21 |
| 2010/0137705 A1* | 6/2010 | Jensen | B82Y 25/00 600/424 |
| 2010/0138183 A1 | 6/2010 | Jensen et al. | |
| 2010/0151587 A1 | 6/2010 | Kojima et al. | |
| 2010/0249201 A1 | 9/2010 | Jensen et al. | |
| 2010/0249571 A1 | 9/2010 | Jensen et al. | |
| 2010/0305427 A1 | 12/2010 | Huber et al. | |
| 2015/0173645 A1 | 6/2015 | Nagarkar et al. | |

\* cited by examiner

METHODS AND SYSTEMS FOR IMPROVED NAVIGATION

BACKGROUND

Embodiments of the present specification relate generally to magnetic sensors, and more particularly to methods and systems for improving noise rejection in magnetic sensors used in surgical navigation systems.

Generally, navigation systems are used to provide position and orientation information corresponding to subjects of interest. Accordingly, navigation systems find use in application areas such as aviation, industrial operations, security, gaming, animation, motion sensing, and/or medical applications. For example, during interventional procedures, a surgical navigation system may be used to assist in rapid and accurate positioning and/or orientation of surgical instruments, implants, or other medical devices in a patient's body.

Specifically, certain surgical navigation systems provide a representation of the medical device in relation to an anatomical region of interest via images generated by an associated imaging system such as an X-ray or ultrasound system. Typically, the generated images may be registered to an overall position and orientation of the patient and/or a target anatomy. Additionally, as the medical device is positioned with respect to the patient anatomy, the images generated by the imaging system may be continually updated to reflect location coordinates for the medical device that are determined using the navigation system. The continually updated images allow a medical practitioner to manipulate the medical device to a desired position and/or orientation in the patient's body.

Certain surgical navigation systems employ electromagnetic sensors to determine a position and/or orientation of the medical device. Particularly, in conventional surgical navigation systems, the electromagnetic sensors may be implemented with coils or microcoils that are attached to the medical device and are configured to generate and/or detect magnetic fields. The navigation system measures a response of the coils to the magnetic field, and in turn, determines a position of the medical device based on the measured response.

Generally, microcoils having large size and/or operating at high frequencies, for example of about several kHz, provide satisfactory tracking information. However, the microcoils exhibit poor signal-to-noise ratio (SNR) and reduced range at lower frequencies and/or volumes. Additionally, the microcoils are susceptible to magnetic field distortions that arise from eddy currents in nearby conducting objects, such as surgical implements or imaging systems. As tracking techniques using microcoil-based navigation systems rely on a stable magnetic field or a known magnetic field map, unpredictable disturbances resulting from movement of metallic objects in the magnetic field reduce accuracy of the tracking technique, often rendering the tracking technique inadequate. Moreover, these microcoils are generally expensive to manufacture.

Accordingly, certain surgical navigation systems offer use of compact and relatively inexpensive magnetic sensors such as Hall-effect sensors, coil sensors, or various magnetoresistive sensors for determining position and/or orientation information. Anisotropic magnetoresistance (AMR) sensors, in particular, can detect fields as low as about $10^{-9}$ Tesla, are extremely small, and are easy to fabricate. AMR sensors, thus, appear particularly suitable for use in navigation systems.

However, when used in surgical navigation systems, cables connecting the AMR sensors to the system electronics often pick up considerable "noise" or interfering signals resulting in erroneous position and/or orientation information. This noise is further amplified due to a high gain amplifier employed to boost the typically low AMR sensor output prior to digitization. As accurately determining position and orientation of the medical device is significant for appropriate administration of treatment and/or for avoiding injury to patient anatomy, the noise in the AMR sensor-based measurements limits use of the AMR sensors in conventional surgical navigation systems.

BRIEF DESCRIPTION

In accordance with certain aspects of the present disclosure, a navigation system, a method for navigation, and non-transitory computer readable medium that stores instructions executable by one or more processors to perform the method are presented. The system includes at least one magnetic sensor operatively coupled to a target device and configured to detect a magnetic field. The system also includes a processing subsystem operatively coupled to the target device via a cable and configured to measure a first response signal received from the magnetic sensor in response to the magnetic field when the magnetic sensor has a reference sensitivity. Moreover, the processing subsystem may be configured to measure a second response signal received from the magnetic sensor in response to the magnetic field when the magnetic sensor has a reversed sensitivity, where the reversed sensitivity is obtained by applying varying voltage and/or frequency configurations to the magnetic sensor while an alignment of one or more magnetic domains corresponding to the magnetic sensor remains unchanged. Additionally, the processing subsystem is configured to determine a useful portion of the first response signal by eliminating common-mode noise from the first response signal based on a difference between the first response signal and the second response signal. Further, the processing subsystem is configured to determine a position of the target device based on the useful portion of the response signal.

In accordance with certain other aspects of the present disclosure, a navigation system, a method for navigation, and non-transitory computer readable medium that stores instructions executable by one or more processors to perform the method for navigation are disclosed. The system includes at least one magnetoresistance sensor operatively coupled to a subject and configured to detect a magnetic field. Additionally, the system includes a processing subsystem operatively coupled to the subject via a cable and configured to apply a bias signal having a desired bias frequency to shift a signal frequency of a response signal of the magnetoresistance sensor that includes common-mode noise. Further, the processing subsystem is configured to determine a useful portion of the response signal of the magnetoresistance sensor by measuring the response signal at a shifted frequency, the shifted frequency being a sum of the signal frequency and the bias frequency. Moreover, the processing subsystem is configured to determine a position of the subject based on the useful portion of the response signal.

In accordance with further aspects of the present disclosure, a method is presented. The method includes providing a magnetoresistance sensor that is operatively coupled to a subject and is configured to measure a magnetic field. One or more magnetic field measurements corresponding to a desired position of the subject are determined while operating the magnetic sensor in two or more different sensitivity settings and/or frequency configurations while an alignment of one or more magnetic domains corresponding to the magnetic sensor remains unchanged. Further, one or more actual magnetic field measurements at the desired position are determined by eliminating common mode noise based on a determined difference between the magnetic field measurements determined at the different sensitivity settings and/or frequency configurations. Subsequently, an accurate position of the subject is determined based on the actual magnetic field measurement.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
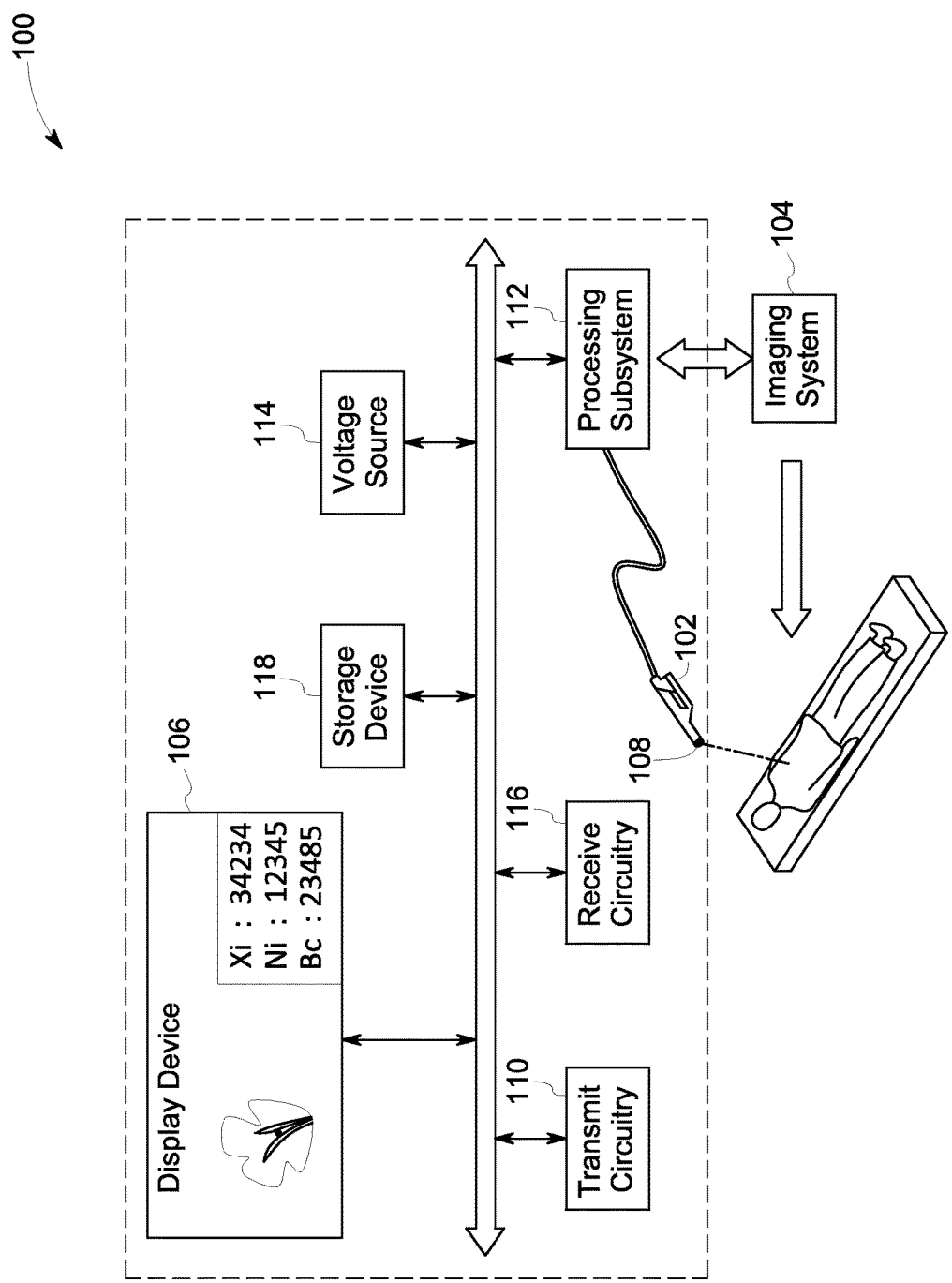
FIG. 1 is a schematic representation of an exemplary navigation system, in accordance with aspects of the present disclosure.

The following description presents systems and methods for improving noise rejection in magnetic sensors. Particularly, certain embodiments illustrated herein describe methods and systems that substantially reduce common-mode noise experienced by magnetic sensors such as coil sensors, giant magnetoresistance (GMR) sensors, semiconducting magnetoresistance (SMR) sensors, and/or anisotropic magnetoresistance (AMR) sensors when used in wired navigation systems. The common-mode noise corresponds to interference that appears on both terminals (signal and circuit return) of the magnetic sensors and ground.

However, typical use of the magnetic sensors, such as in cellphones and compass applications, results in very little common-mode noise due to proximity of the magnetic sensors to associated processing electronics. Certain other systems are known to mitigate the common-mode noise by transmitting a plurality of pulses of opposite polarity (such as Set/Reset pulses) per second to the magnetic sensor to reverse sensitivity of corresponding response signals. Specifically, such systems may reverse sensitivity of the response signals to magnetic fields indirectly by reversing a sensor poling, thereby reducing the common-mode noise as well as improving absolute measurements of fixed or unchanging magnetic fields. However, such conventional approaches for mitigating common-mode noise in magnetoresistance sensors may not be suitable for all position tracking applications.

By way of example, when used in a surgical navigation system, a magnetic sensor may suffer from considerable common-mode noise. Particularly, inventors of the present disclosure realized that the common-mode noise substantially distorts position and/or orientation measurements corresponding to a medical device when the magnetic sensors are separated from processing electronics in a surgical navigation system by more than a determined distance. The resulting distortion limits performance of the magnetic sensors in conventional surgical tracking systems. Moreover, even the conventional approach of reversing sensitivity of the response signals of the magnetic sensors to mitigate the common noise is unsuitable for use in surgical applications as it requires repeated transmission of high voltage pulses that raise leakage current and heating concerns.

Inventors of the present disclosure, thus, realized a need for substantial reduction in the common-mode noise experienced by the magnetoresistance sensors of a specified size and/or type when separated from processing electronics by more than a determined distance, for example, of about 12 inches. Accordingly, embodiments described herein present methods and systems configured to vary a bridge voltage used in a magnetic sensor to produce a corresponding variation in the resulting response signal, while a common-mode noise in the response signal remains constant. This common-mode noise may then be eliminated from the response signals based on a determined difference between magnetic field measurements that are determined when operating the magnetic sensor at different sensitivity settings and/or frequency configurations while an alignment of one or more magnetic domains corresponding to the magnetic sensor remains unchanged.

To that end, the magnetic sensor may be operated at different sensitivity settings, for example, by using a time varying bridge voltage, doubling the bridge voltage, and/or reversing polarity of the bridge voltage used in operation of the magnetic sensor. Alternatively, the sensitivity of the magnetic sensor may be varied by changing a degree of poling of the magnetic sensor material, using a current-controlled differential pre-amplifier stage that allows for control of sensor gain, and/or by using any other known method suitable for varying the sensitivity of the magnetic sensor without changing the alignment of one or more magnetic domains corresponding to the magnetic sensor.

For clarity, the following description is discussed with reference to reducing noise in AMR sensor measurements. However, certain embodiments of the present methods and systems may be implemented in connection with other magnetic sensors such as coil sensors, three-dimensional (3D) Hall-effect-based sensors, SMR sensors, and/or GMR sensors. Furthermore, embodiments of the present disclosure may also be used in other medical and/or non-medical applications such as position and/or orientation tracking systems, electronic compasses, automotive wheel speed and crankshaft sensing system, vehicle navigation, current sensing, voltage sensing, and/or switching subsystems. An exemplary environment that is suitable for practicing various implementations of the present system is described in the following sections with reference to FIG. 1.

FIG. 1 illustrates an exemplary navigation system 100 for use in tracking position and/or orientation of a subject in real-time. For discussion purposes, the system 100 is described with reference to a surgical navigation system.

Accordingly, in one embodiment, the subject corresponds to a surgical tool such as a needle, an endoscope, or a catheter 102 adapted for use in a confined medical or surgical environment such as a body cavity, orifice, or a blood vessel. Generally, during an interventional procedure, the catheter 102 is advanced within a vascular structure such as a blood vessel of a patient for imaging surrounding tissues. The resulting images find use in diagnosis, and/or for providing therapy to one or more target locations within the patient's body.

However, insertion and movement of the catheter 102 within a blood vessel is a challenging procedure. Accordingly, in certain embodiments, the catheter 102 may be communicatively coupled to an associated imaging system 104 such as a computed tomography (CT) system, a magnetic resonance imaging (MRI) system, an ultrasound imaging system, an X-ray system, and/or a positron emission tomography (PET) system. In one embodiment, the imaging system 104 may be configured to visualize the catheter 102 and/or the blood vessel on a display device 106 in real-time. The real-time visualization allows for guided navigation of the catheter 102 through the blood vessel, thus aiding in preventing injury to surrounding tissues.

It may be noted that although the present embodiment is described with reference to tracking movement of the catheter 102 through a blood vessel, certain embodiments of the navigation system 100 may be used to track movement of a subject through other biological tissues of the patient such as lymph vessels, cerebral vessels, hepatic vessels, and/or renal vessels. Certain other embodiments of the navigation system 100 may be also used to track movement of a subject in non-medical environments such as during industrial evaluation and/or vehicle navigation.

Particularly, in a presently contemplated embodiment, the navigation system 100 employs one or more magnetic sensors for use in detecting a position and/or orientation of the catheter 102 during an interventional surgical procedure. The magnetic sensors, for example, may include a coil sensor, a Hall-effect-based sensor, an SMR sensor, an AMR sensor, and/or a GMR sensor. Although, more than one kind of magnetic sensor may be used in different embodiments of the navigation system 100, the present disclosure is described with reference to the use of the AMR sensor 108 for detecting a position and/or orientation of the catheter 102 during the interventional procedure. To that end, the AMR sensor 108 may be operatively coupled, for example through mechanical means, to a tip of the catheter 102. Specifically, a change in resistance of the AMR sensor 108 under influence of an external magnetic field may be used to determine a position and/or orientation of the catheter 102.

Accordingly, in one embodiment, the system 100 includes transmit circuitry 110 configured to generate the magnetic field having a desired magnitude and/or direction. The transmit circuitry 110, for example, may include a magnet, a current carrying wire, one or more radiofrequency (RF) coils, and/or other such devices suitable for generating the desired magnetic field within an operating range of the AMR sensor 108.

Additionally, in certain embodiments, the system 100 includes a processing subsystem 112 configured to control one or more parameters corresponding to the generation of the magnetic field by the transmit circuitry 110. For example, in one embodiment, the processing subsystem 112 may be configured to transmit appropriate control signals to the transmit circuitry 110 for generation of a magnetic field having a constant magnitude and/or direction relative to the AMR sensor 108. The AMR sensor 108, in turn, may be configured to generate one or more response signals indicative of a detected change in magnitude and/or direction of the magnetic field as the catheter 102 including the AMR sensor 108 moves across different locations in the patient's body.

In certain embodiments, the processing subsystem 112 amplifies and/or digitizes response signals for use in determining position information corresponding to the AMR sensor 108, and in turn, the catheter 102. To that end, the processing subsystem 112, for example, includes one or more general-purpose or application-specific processors, digital signal processors, microcomputers, microcontrollers, Application Specific Integrated Circuits (ASICs), and/or Field Programmable Gate Arrays (FPGA).

According to certain aspects of the present disclosure, the processing subsystem 112 uses the digitized information to determine a change in magnitude and/or angle of the detected magnetic field as the catheter 102 including the AMR sensor 108 advances through a blood vessel. In one embodiment, the change in angle of the magnetic field may be indicative of an angular position of the AMR sensor 108 relative to a reference position (for example, the transmit circuitry 110). In an alternative embodiment, however, any other determined relationship between detected magnetic field and the AMR sensor 108 may be used to determine the position and/or orientation of the AMR sensor 108 and/or the catheter 102.

Although the AMR sensor 108 may be configured to provide predictable outputs when subjected to a desired magnetic field, the AMR sensor 108 may pick up considerable noise or interference along a length of a cable corresponding to the catheter 102 that connects the AMR sensor 108 to the processing subsystem 112. This noise may be further amplified if the system 100 employs a high gain amplifier (not shown) to boost the typically low AMR response signal prior to digitization. As previously noted, the noise corresponds to a common-mode noise signal that carries no useful information. For example, when operating the surgical navigation system 100, a common-mode noise signal ranging from a few microvolts to tens of millivolts may appear along the length of a connecting cable in the catheter 102 after amplification. This common-mode noise signal may significantly distort the AMR response signal, thereby leading to erroneous position and/or orientation measurements unsuitable for use in surgical navigation.

Accordingly, the processing subsystem 112 may be configured to control operation of the system 100 so as to mitigate ill effects of the common-mode noise signal on the position and/or orientation measurements. Particularly, in one embodiment, the processing subsystem 112 may be configured to vary a bridge voltage of the AMR sensor 108 to produce a corresponding variation in the AMR response signal. Typically, the common-mode noise signal varies with relative locations of the connecting cable of the catheter 102 and the AMR sensor 108, but does not depend on the bridge voltage of the AMR sensor 108. The frequency, amplitude, and phase of the common-mode noise signal, thus, remains unchanged even under the influence of varying bridge voltages.

Accordingly, in certain embodiments, the constant frequency of the common-mode noise signal may be used to identify and eliminate the common-mode noise signal from the AMR response signal. For example, the common-mode noise signal may be eliminated by using a time varying bridge voltage, doubling the bridge voltage, and/or directly or indirectly reversing sensitivity of the bridge voltage used in operation of the AMR sensor 108. To that end, in one embodiment, the system 100 may include a voltage source 114 configured to provide varying voltages to the AMR sensor 108 based on control signals received from the processing subsystem 112. The voltage source 114, for example, may be a battery operated power source, a direct current source, and/or an alternating current source.

In one embodiment, the voltage source 114 may be configured to supply varying voltages to the AMR sensor 108 such that the resulting AMR response signals may alternately have positive and negative sensitivities for determining each magnetic field measurement. Alternatively, the voltage source 114 may be configured to apply a desired bias voltage to the AMR sensor 108 to shift a signal frequency of the AMR response signals by a determined value. As previously noted, the common-mode noise signal remains unchanged in both of these embodiments despite use of the varying bridge voltages or the bias voltage.

Furthermore, in certain embodiments, the system 100 may include receive circuitry 116 configured to receive the AMR response signals generated by the AMR sensor 108 in response to the varying bridge and/or bias voltages. The AMR response signals, for example, may correspond to output voltage values indicative of a change in resistance of AMR sensor material. The change in resistance, in turn, may be used by the processing subsystem 112 to detect changes in strength and/or direction of the magnetic field at different points as the catheter 102 including the AMR sensor 102 is advanced through the blood vessel.

Accordingly, in one embodiment, the receive circuitry 116 digitizes the AMR response signals and transmits the digitized information to a storage repository 120 for later processing. The storage repository 120, for example, includes a random access memory, a read only memory, a disc drive, solid-state memory device, and/or a flash memory configured to store the AMR response signals and/or the digitized information. Alternatively, the receive circuitry 116 communicates the AMR response signals to the processing subsystem 112 in real-time for digitization and/or further processing.

As previously noted, the processing subsystem 112 uses the digitized information for determining a position and/or orientation of the catheter 102 with greater accuracy. In one embodiment, for example, the processing subsystem 112 uses the digitized information to compute a difference between the AMR response signals having alternately positive and negative sensitivity settings for determining each magnetic field measurement. Specifically, in one example, subtracting the AMR response signals having opposite sensitivity settings eliminates the common-mode noise signal that is unaffected by a change in the bridge voltage of the AMR sensor 108, while retaining the useful portion of the AMR response signals for use in accurate magnetic field measurements. The magnetic field measurements, in turn, may be used to identify an accurate position and/or orientation of the catheter 102 within the patient's body, for example, using a predetermined correlation. Certain exemplary methods for eliminating common-mode noise from the AMR response signals for improved surgical navigation will be described in greater detail with reference to FIGS. 2-7.

Further, in certain embodiments, the processing subsystem 122 uses the useful portion of the AMR response signals to allow for real-time update of the position and orientation of the catheter 102 on the display device 106. As previously noted, the position and orientation information determined by the processing subsystem 122 may be registered to the same position coordinate system as the images generated by the imaging system 104. Accordingly, the processing subsystem 112 may be configured to simultaneously update visualization of the catheter 102 relative to the surrounding tissues as the catheter 102 advances within the patient's body. The resulting visualization on the display device 106 allows a medical practitioner to manipulate the catheter 102 to a desired position and/or orientation in the patient's body with greater accuracy. Alternatively, in certain embodiments, the processing subsystem 112 may be configured to provide navigational guidance to the medical practitioner through audio and/or visual instructions.

Embodiments of the system 100, thus allow for significant improvement in navigational guidance available to the medical practitioner during surgical procedures. Particularly, use of the AMR sensor 108 allows fabrication of smaller, easy to manufacture, highly sensitive, and cost-effective surgical navigation systems. Additionally, operating the AMR sensor 108 using varying bridge voltages eliminates the common-mode noise, thereby providing accurate position and orientation information for use in real-time surgical navigation. An exemplary method for improved surgical navigation will be described in greater detail with reference to FIG. 2.

Figure 2:
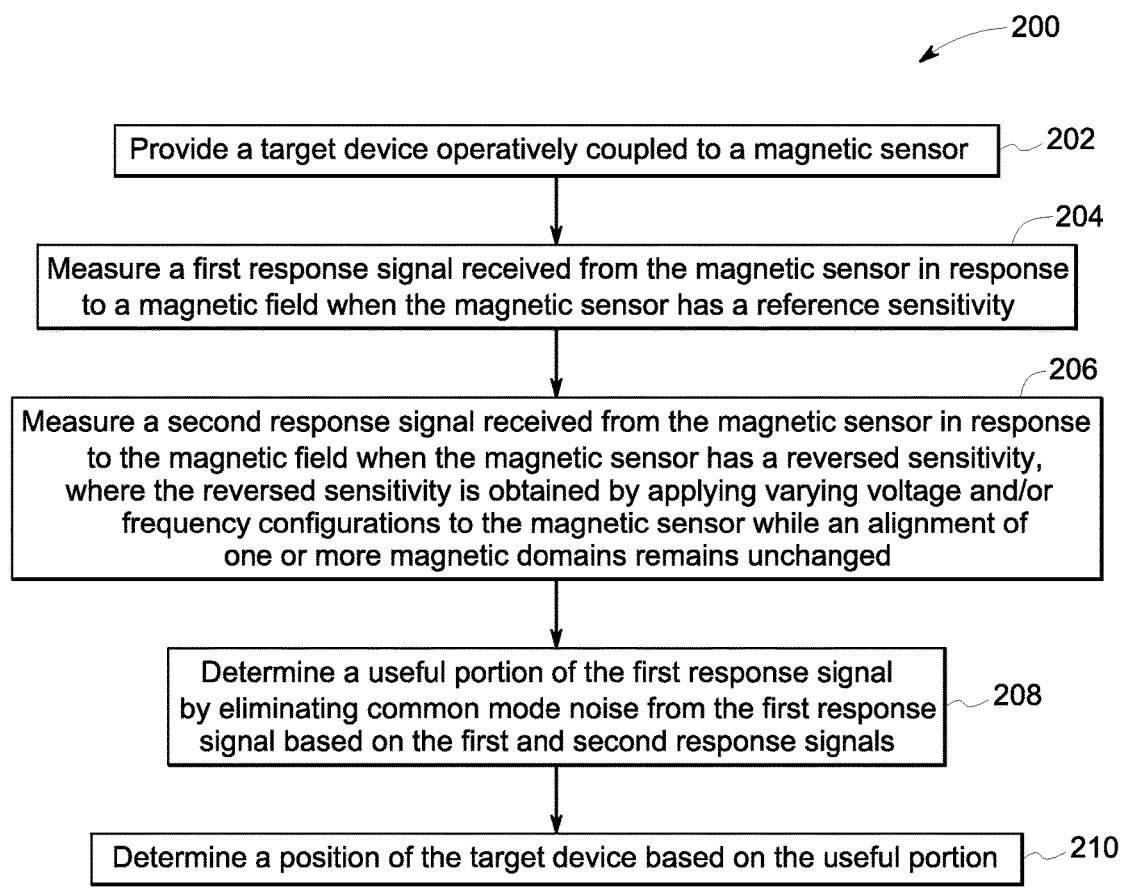
FIG. 2 is a flow diagram illustrating an exemplary method for improving noise rejection in magnetic sensors used in navigation systems, in accordance with aspects of the present disclosure.

FIG. 2 illustrates a flowchart 200 depicting an exemplary method for improving noise rejection in magnetic sensors used in navigation systems. The exemplary method may be described in a general context of computer executable instructions stored and/or executed on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 2, the exemplary method is illustrated as a collection of blocks in a logical flow chart, which represents operations that may be implemented in hardware, software, or combinations thereof. The various operations are depicted in the blocks to illustrate the functions such as measuring a response signal received from the magnetic sensor, eliminating common-mode noise, and determining a position of the target device corresponding to the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of the navigation system 100 of FIG. 1. However, the present method may also be used to improve noise rejection in various other medical and/or non-medical systems that employ magnetic sensors.

The method begins at step 202, where a target device operatively coupled to a magnetic sensor is provided. In one embodiment, the target device corresponds to a catheter such as the catheter 102 of FIG. 1. Further, the magnetic sensor corresponds to a GMR sensor, an SMR sensor, a Hall-effect sensor, a coil sensor, and/or an AMR sensor such as the AMR sensor 108 of FIG. 1. In certain embodiments, the magnetic sensor is configured to operate in a magnetic field such that the magnetic sensor provides response signals indicative of a change in one or more characteristics of the magnetic field as the target device is being advanced through a blood vessel. The magnetic field characteristics, for example, include a magnitude, a direction, and/or an angular orientation of the magnetic field.

In certain embodiments, the magnetic sensor may include a resistive bridge circuit, which may be operated at different bridge voltages to allow for identification and elimination of common-mode noise from the resulting response signals. Specifically, in one embodiment, a voltage source such as the voltage source 114 of FIG. 1 may be configured to provide a first contact of the magnetic sensor with a positive voltage for a first period of time to operate the magnetic sensor in a reference sensitivity. Further, the voltage source may be configured to provide a negative voltage to a second contact of the magnetic sensor to operate the magnetic sensor in reversed sensitivity for a second period of time. Alternatively, the sensitivity of the response signals received from the magnetic sensor may be switched, for example, using an analog-to-digital converter present in a surgical navigation system.

Moreover, at step 204, a first response signal received from the magnetic sensor in response to the magnetic field when the magnetic sensor has a reference sensitivity may be measured. Specifically, in one embodiment, the first response signal may be measured when the voltage across the bridge circuit in the magnetic sensor has positive sensitivity or polarity (for example, +1 Volt). Additionally, at step 206, a second response signal received from the magnetic sensor in response to the magnetic field when the magnetic sensor has a reversed sensitivity may be measured. Particularly, the reversed sensitivity may be obtained by applying varying voltage and/or frequency configurations to the magnetic sensor while an alignment of one or more magnetic domains corresponding to the magnetic sensor remains unchanged. Accordingly, in one example, the second response signal may be measured when the voltage across the bridge circuit has negative sensitivity or polarity (for example, −1 Volt). In certain embodiments, the first and second response signals may be acquired at a desired position in the patient anatomy while being advanced or retracted from the blood vessel. However, as previously noted, the first and second response signals may be distorted due to presence of a common-mode noise signal, thus resulting in erroneous magnetic field measurements that lead to inaccurate position information.

Accordingly, at step 208, a useful portion of the first response signal may be determined by eliminating common-mode noise from the first response signal based on a difference between the first and second response signals. As previously noted, the first and second response signals are received as output from the magnetic sensor operating at reference (for example, +5V) and reversed sensitivity settings (−5V), respectively. Accordingly, in one example, a difference between the measured values of the first and second response signals may be computed. The computed difference eliminates the common-mode noise component, which remains at reference sensitivity in both the first and second response signals, while retaining the useful portions of the first and second response signals. An exemplary method for eliminating the common-mode noise and determining the useful portion of the response signals received as output from the magnetic sensor will be discussed in greater detail with reference to FIG. 3.

Further, at step 210, a position of the target device may be determined based on the useful portion of the first response signal. As previously noted, measuring the response signals at alternating bridge voltages having the reference and reversed sensitivity settings eliminates the common-mode noise, while retaining, for example, twice of the useful signal. Half of the retained signal, thus, provides an indication of the actual response of the magnetic sensor indicative of an accurate magnetic field measurement at a desired position. Use of the accurate magnetic field measurement in turn, may allow for more accurate tracking of position and orientation of the target device, thereby aiding in navigational guidance.

Figure 3:
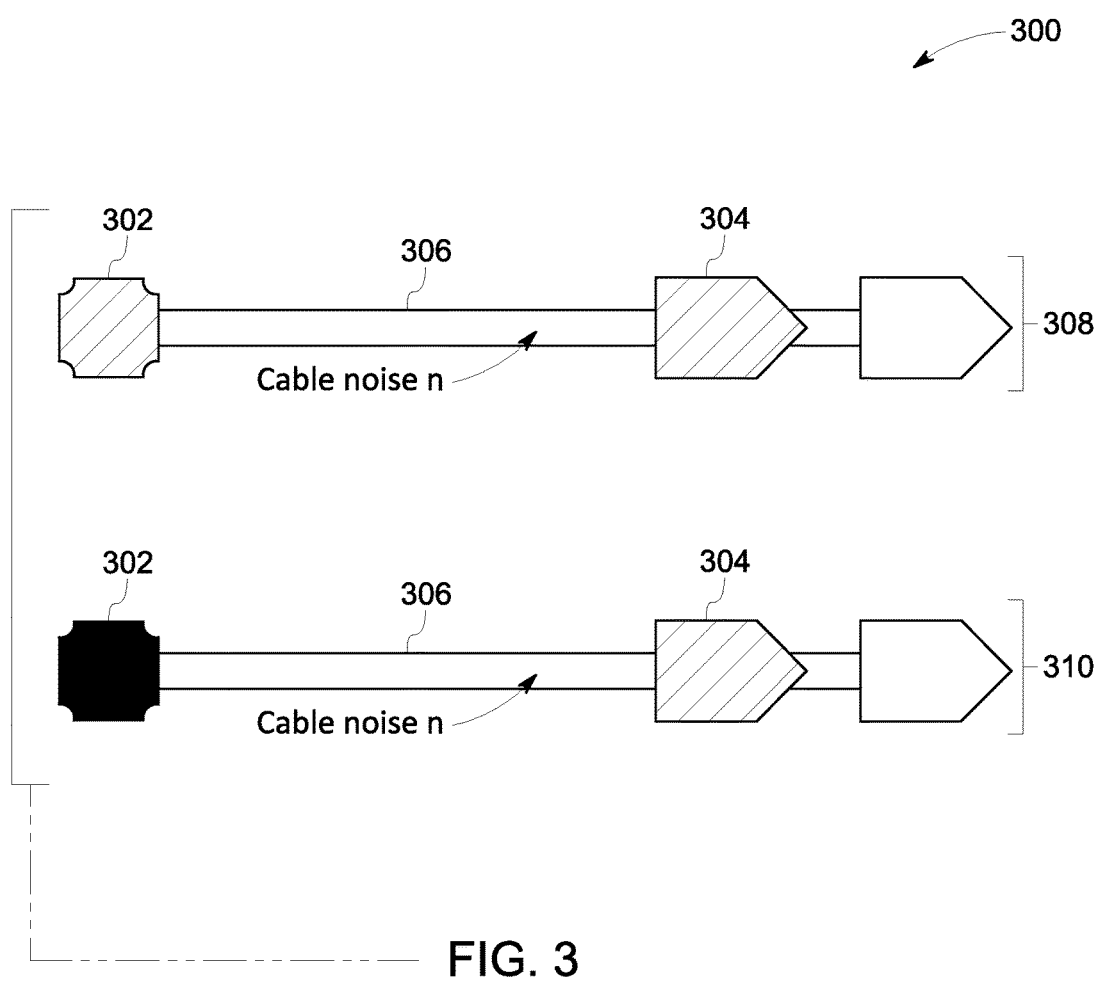
FIG. 3 is a schematic representation of the exemplary method of FIG. 2.

FIG. 3 depicts a schematic representation 300 of an embodiment of the exemplary method of FIG. 2. In the embodiment illustrated in FIG. 3, the magnetic sensor 302 is operationally coupled to processing electronics 304 through a cable 306. The processing electronics 304, for example, corresponds to the processing subsystem 112 of FIG. 1. Further, reference numeral 308 is representative of an operational state of the magnetic sensor 302 configured to operate under the influence of a reference bias voltage. When the magnetic sensor 302 is operational, the cable 306 may behave like an antenna and pick up stray currents along the length of the cable 306. These stray currents may give rise to a common-mode noise signal that generates magnetic and/or electromagnetic fields with equal magnitude and polarity as the response of the magnetic sensor 302 to the magnetic field. Accordingly, eliminating the common-mode noise signal from the magnetic field measurements is often a challenging process. Therefore, a first response signal received as output from the magnetic sensor 302 in response to an external magnetic field at a desired position may be represented, for example, using equation (1):

$$U_1 = S + nG \qquad (1)$$

where $U_1$ corresponds to the first response signal, S corresponds to the useful portion of the first response signal $U_1$, n corresponds to noise, G corresponds to the gain, and nG corresponds to the common-mode noise in the navigation system such as the system 100 of FIG. 1.

Further, reference numeral 310 is representative of an operational state of the magnetic sensor 302 configured to operate under the influence of a reversed bias voltage. In one embodiment, the reversed bias voltage has the same magnitude but opposite direction as the reference bias voltage. Particularly, the reversed bias voltage reverses the sensitivity of the AMR bridge voltage, and in turn, the sensitivity of the AMR response signals received in response to a detected change in the external magnetic field. However, as previously noted, the common-mode noise in the system, being independent of the bridge voltage, remains unchanged. Accordingly, a second AMR response signal $U_2$ received in response to the external magnetic field at the desired position may be represented, for example, using equation (2):

$$U_2 = -S + nG \qquad (2)$$

Subsequently, a difference between values of the equations (1) and (2) may be computed. The computed difference, for example, may be represented using equation (3):

$$U_1 - U_2 = (S + nG) - (-S + nG) = 2S \qquad (3)$$

As evident from equation (3), subtracting the response signals received from the magnetic sensor operating at different sensitivity settings eliminates the common-mode noise component, thereby providing more accurate information for position and/or orientation determination.

Figure 4:
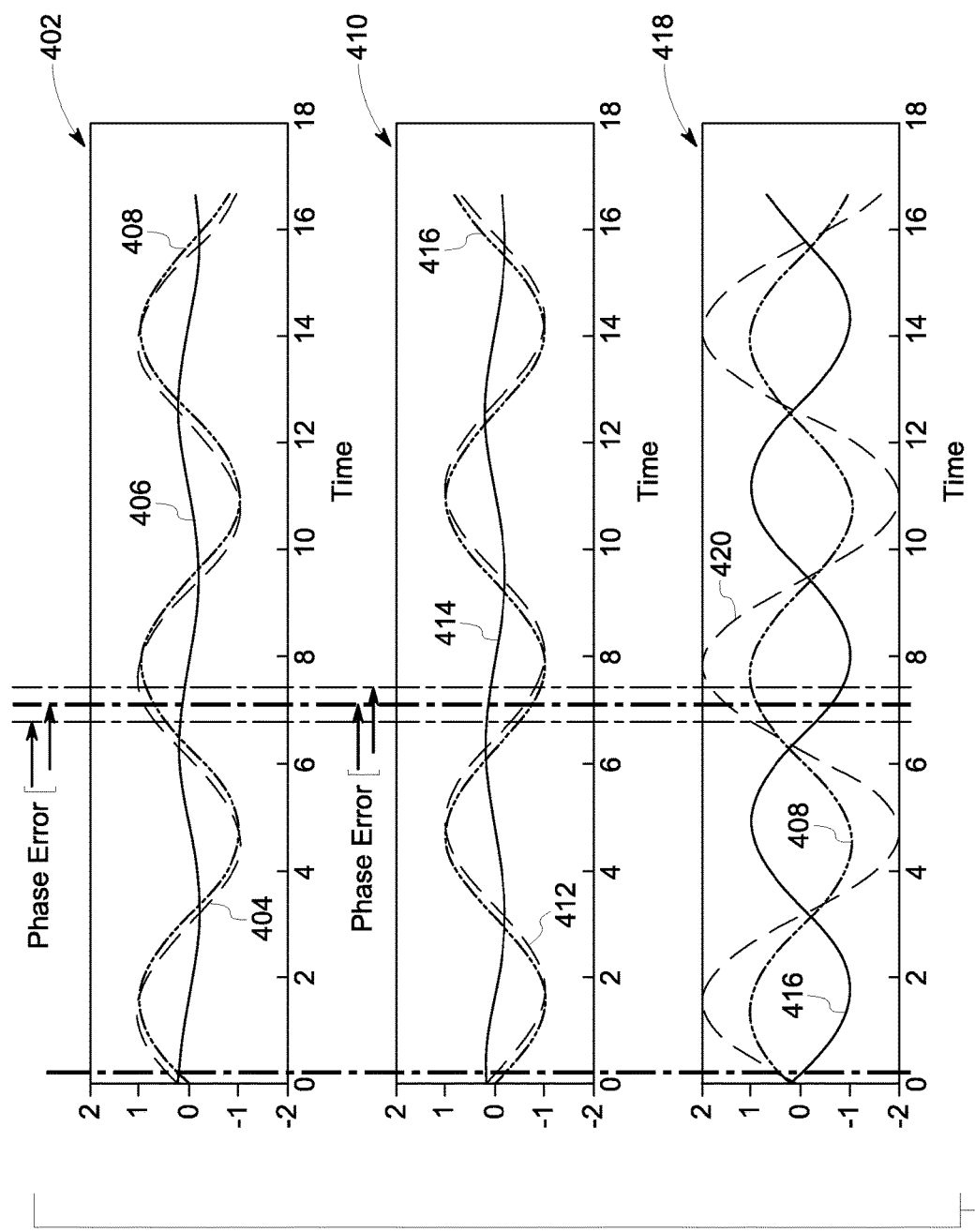
FIG. 4 is a graphical representation of an exemplary sequence of processing the response signals received from a magnetic sensor using the method of FIG. 2.

Further, FIG. 4 illustrates an exemplary sequence of processing the response signals received as output from the magnetic sensor using the method of FIG. 2 for alleviating common-mode noise. In FIG. 4, a first graphical representation 402 is indicative of a measurement of a response signal at a bridge voltage having a reference sensitivity setting. Particularly, in the graphical representation 402, a reference numeral 404 is representative of a first response signal measured at the reference sensitivity setting, for example, when a bridge voltage is of about +5 Volts. Additionally, the reference numerals 406 and 408 are representative of the noise and the useful portion, respectively, determined from the measured response signal 404.

As previously noted, the measured response signal 404 corresponds to the output signals received from a magnetic sensor in response to an externally applied magnetic field. Moreover, the noise may correspond to a common-mode noise signal picked up by a cable connecting the magnetic sensor to processing electronics in a navigation system, whereas the useful portion of the response signal 408 corresponds to the actual or expected response of the magnetic sensor in absence of the common-mode noise. As evident from the depictions of the graphical representation 402, the measured response signal 404 is shifted away from the actual response signal 408, thereby indicating a phase error.

Additionally, in a second graphical representation 410, a reference numeral 412 is representative of a second response signal measured at reversed sensitivity, for example, at a bridge voltage of about −5 Volts. Additionally, the reference numerals 414 and 418 are representative of the noise and the actual magnetic response signal, respectively, determined from the response signal measured at the reversed sensitivity setting. As evident from the depictions of the graphical representation 410, the measured magnetic response signal 412 is shifted away from the actual response signal 416, thereby indicating a phase error.

Further, a third graphical representation 418 depicts representations of the response signals 408 and 416 measured at bridge voltages having reference and reversed sensitivity settings, respectively. Moreover, in FIG. 4, a reference numeral 420 is representative of a difference between the response signals 408 and 416. As evident from the depictions of the graphical representation 418, computing the difference between the response signals 408 and 416 eliminates the common-mode noise signal. Moreover, the resulting signal 420 matches the phase of the actual response signal devoid of any common-mode noise, thus indicating accuracy of the position measurements determined using embodiments of the present method.

Figure 5:
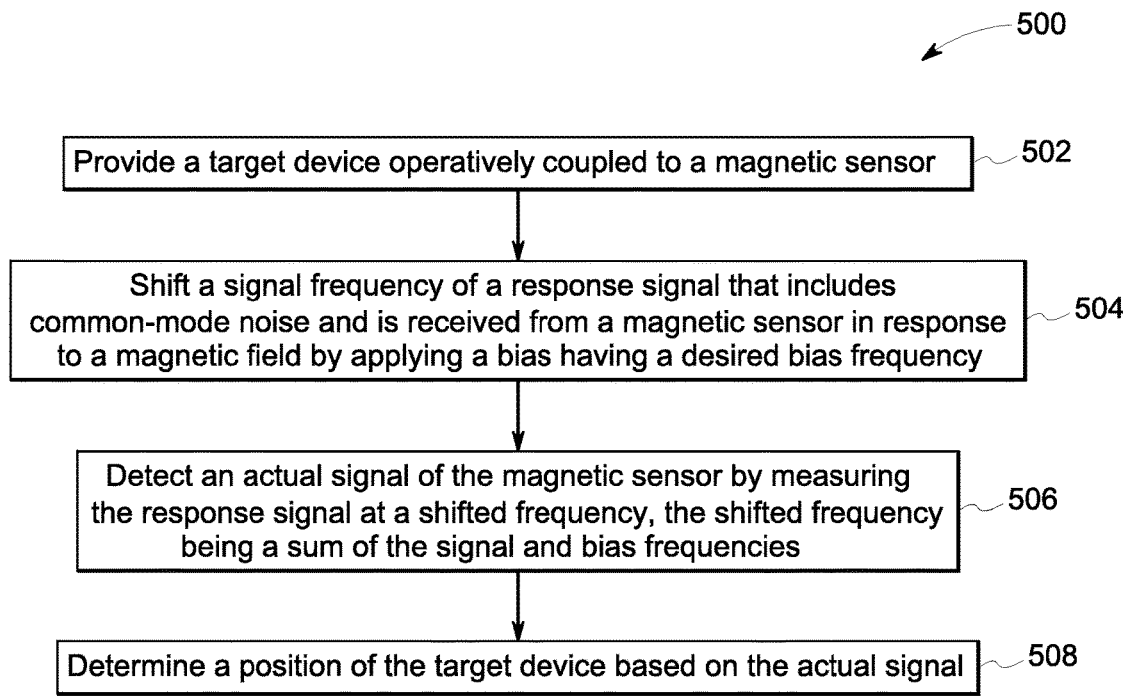
FIG. 5 is a flow diagram illustrating another exemplary method for improving noise rejection in magnetic sensors, in accordance with aspects of the present disclosure.

Further, FIG. 5 illustrates a flow chart 500 depicting another exemplary method for improving noise rejection in magnetic sensors. The method begins at step 502, where a target device operatively coupled to a magnetic sensor is provided. The target device, for example, may correspond to a catheter, whereas the magnetic sensor, for example, may correspond to one or more AMR, SMR, GMR, coil-based, and/or other suitable magnetic sensors. In one embodiment, a magnetic sensor is attached to a tip of the catheter such that a determined position of the magnetic sensor may be indicative of a distal end of the catheter.

As previously noted, measurements derived from the response signals received from a magnetic sensor may not be accurate owing to the presence of common-mode noise in the navigation system. Accordingly, at step 504, a signal frequency of a response signal, which includes common-mode noise and is received from a magnetic sensor in response to a magnetic field, is shifted by applying a bias signal having a desired bias frequency. The bias signal, for example, may correspond to a time varying signal such as a sinusoidal signal, a square wave signal, or a triangular wave signal.

At step 506, a useful portion of the response signal of the magnetic sensor may be detected by measuring the response signal of the magnetic sensor at a shifted frequency, the shifted frequency being a sum of the signal and bias frequencies. For example, in one embodiment, instead of detecting response signals having an original signal frequency of about 100 Hertz (Hz), application of a signal having a bias frequency of about 1 Kilohertz (KHz) causes the magnetic sensor to detect the response signals at a shifted frequency of about 1.1 KHz. However, common-mode noise signals, being independent of the applied bias, continue to appear at a frequency of about 100 Hz. Thus, only the useful portion of the response signal is shifted in the frequency spectrum, while the frequency of the common-mode noise signals remains unchanged.

Subsequently, at step 508, a position of the target device may be determined based on the useful portion of the response signal. In certain embodiments, the position and/or orientation of the magnetic sensor, and in turn, the catheter may be determined as previously described with reference to FIGS. 1-2. Specifically, the magnetic field measurements derived from the useful portion of the response signals may be used to identify a position and/or orientation of the target device, thus aiding in providing navigational guidance.

Figure 6:
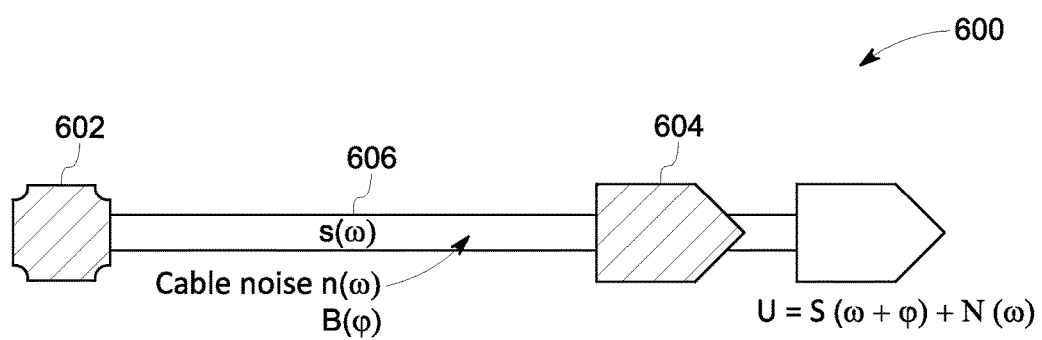
FIG. 6 is a schematic representation of the exemplary method of FIG. 5.

Further, FIG. 6 depicts a schematic representation 600 of an embodiment of the exemplary method of FIG. 5. In the embodiment illustrated in FIG. 6, a magnetic sensor 602 is operationally coupled to processing electronics 604 of a navigation system through a cable 606. The processing electronics 604, for example, may be configured to perform one or more of the functions as described with reference to the processing subsystem 112 of FIG. 1. Further, reference numeral 608 is representative of an operational state of the magnetic sensor 602 configured to operate under the influence of a time varying bias voltage. As previously noted, the cable 606 may behave like an antenna and pick up stray currents along the length of the cable 606 during operation. These stray currents may give rise to common-mode noise signals that may distort the AMR response signals.

Accordingly, an embodiment of the method described with reference to FIG. 5 may be implemented to eliminate the common-mode noise in a single step. Specifically, in one embodiment, a bias signal having a desired bias frequency may be applied to a bridge circuit in the magnetic sensor to shift a signal frequency ω of a corresponding response signal by a determined value. An example of a response signal (S(ω)) shifted by a bias frequency φ may be represented using equation (4).

$$U=S(\omega+\varphi)+N(\omega) \qquad (4)$$

where N(ω) corresponds to the common-mode noise detected at the signal frequency ω.

As previously noted, the frequency ω of the common-mode noise signal N existing in the navigation system remains unchanged despite application of the bias signal. The determined value, thus, may be selected such that there is sufficient separation between the original frequency ω and shifted frequency (ω+φ) to allow for accurate measurement of the actual response signal at the shifted frequency. Specifically, use of the bias frequency segregates the useful portion of the response signal and the common-mode noise to different positions over the frequency spectrum. The processing electronics 604, thus, may be configured to measure the useful portion of the response signal independently at the shifted frequency (ω+φ), effectively eliminating the effects of the common-mode noise on the position measurements.

It may be noted that the embodiments for operating the magnetic sensor at different sensitivity settings and/or frequency configurations depicted in FIGS. 2 and 5 for eliminating common-mode noise based on differences between corresponding magnetic field measurements are only exemplary. In alternative embodiments, other suitable methods that vary the sensitivity and/or frequency configuration of the magnetic sensor for use in eliminating common-mode noise from the response signals may be employed. Accurate position and/or orientation measurements determined from the response signals in absence of common-mode noise substantially enhance an accuracy of real-time surgical navigation systems. An exemplary performance of an embodiment of the present methods will be described in greater detail with reference to FIG. 7.

Figure 7:
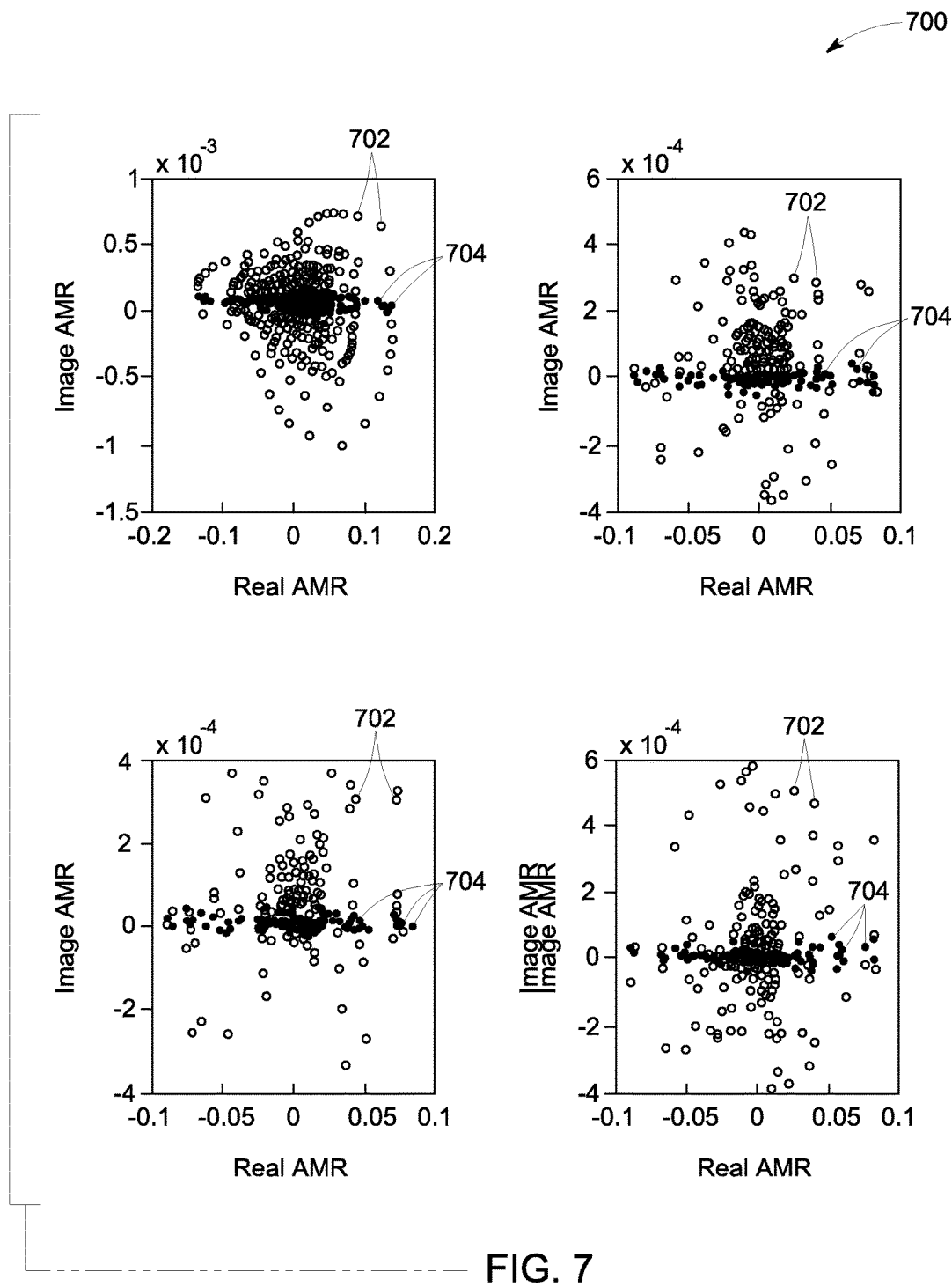
FIG. 7 is graphical representation of measured and actual response signals determined for different frequencies using the method of FIG. 2, in accordance with aspects of the present disclosure.

FIG. 7 illustrates a plurality of graphical representations 700 depicting measured and actual response signals determined for four different frequencies of an externally applied magnetic field, which varies at different locations in space. In the graphical representations depicted in FIG. 7, the real and imaginary parts of the Fourier transform of the response signals are shown with a nominal phase angle of zero. In an ideal scenario, measured data is oriented along the x-axis. Accordingly, the data positioned off of the x-axis is determined to include phase distortion. Specifically, reference numeral 702 is indicative of data corresponding to the position information determined from the detected AMR response signals prior to any common-mode noise rejection. In contrast, reference numeral 704 is indicative of data corresponding to the position information depicting a substantially reduced phase error by employing the method of FIG. 2.

As evident from the depictions of FIG. 7, embodiments of the present methods and systems alleviate signal distortion owing to common-mode noise, thereby allowing for more accurate position and orientation measurements. Accurate position measurements, in turn, provide a significant improvement in navigational guidance available to a medical practitioner during surgical procedures, thus reducing procedure time, while also helping to prevent injury to the patient. Additionally, use of small magnetic sensors such as the AMR or SMR sensors allows fabrication of smaller, easy to manufacture, and cost-effective surgical navigation systems that exhibit substantially greater metal tolerance that conventional coil-based navigation systems.

It may be noted that although specific features of various embodiments of the present systems and methods may be shown in and/or described with respect to only certain drawings and not in others, this is for convenience only. It is to be understood that the described features, structures, and/or characteristics may be combined and/or used interchangeably in any suitable manner in the various embodiments, for example, to construct additional assemblies and techniques. Furthermore, the foregoing examples, demonstrations, and process steps, for example, those that may be performed by the processing subsystem 112, imaging system 104, transmit circuitry 110, and receive circuitry 116 may be implemented by a single device or a plurality of devices using suitable code on a processor-based system.

It should also be noted that different implementations of the present disclosure may perform some or all of the steps described herein in different orders or substantially concurrently, that is, in parallel. In addition, the functions may be implemented in a variety of programming languages, including but not limited to Python, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by a processor-based system to execute the stored code.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A navigation system, comprising:
    at least one magnetic sensor operatively coupled to a target device and configured to detect a magnetic field; and
    a processing subsystem operatively coupled to the target device via a cable and configured to:
        measure a first response signal received from the magnetic sensor in response to the magnetic field when the magnetic sensor has a reference sensitivity;
        measure a second response signal received from the magnetic sensor in response to the magnetic field when the magnetic sensor has a reversed sensitivity, wherein the reversed sensitivity is obtained by applying varying voltage configurations, frequency configurations, or a combination thereof to the magnetic sensor while an alignment of one or more magnetic domains corresponding to the magnetic sensor remains unchanged;
        determine a useful portion of the first response signal by eliminating common-mode noise from the first response signal based on a difference between the first response signal and the second response signal; and
        determine a position of the target device based on the useful portion of the response signal.

2. The system of claim 1, wherein the magnetic sensor comprises a magnetoresistance sensor, a hall-effect sensor, an anisotropic magnetoresistance sensor, a giant magnetoresistance sensor, a coil sensor, or combinations thereof.

3. The system of claim 1, wherein the target device comprises a catheter, a surgical needle, a transducer probe, or combinations thereof.

4. The system of claim 1, further comprising a display device operatively coupled to the processing subsystem and configured to display the determined position of the target device in real-time.

5. The system of claim 1, further comprising a voltage source operatively coupled to the magnetic sensor and configured to:
    provide a positive voltage and a negative voltage to first and second contacts of the magnetic sensor, respectively, to operate the magnetic sensor in the reference sensitivity during a first period of time; and
    provide a negative voltage and a positive voltage to the first and second contacts of the magnetic sensor, respectively, to operate the magnetic sensor in the reversed sensitivity during a second period of time.

6. A method for navigation, comprising:
measuring a first response signal received from at least one magnetic sensor in response to a magnetic field when the magnetic sensor has a reference sensitivity, wherein the magnetic sensor is operatively coupled to a target device;
measuring a second response signal received from the magnetic sensor in response to the magnetic field when the magnetic sensor has a reversed sensitivity, wherein the reversed sensitivity is obtained by applying varying voltage configurations, frequency configurations, or a combination thereof to the magnetic sensor while an alignment of one or more magnetic domains corresponding to the magnetic sensor remains unchanged;
determining a useful portion of the first response signal of the magnetic sensor by eliminating common-mode noise from the first response signal based on a difference between the first response signal and the second response signal; and
determining a position of the target device based on the useful portion of the first response signal.

7. The method of claim 6, further comprising:
providing a positive voltage and a negative voltage to first and second contacts of the magnetic sensor, respectively, to operate the magnetic sensor in the reference sensitivity during a first period of time; and
providing a negative voltage and a positive voltage to the first and second contacts of the magnetic sensor, respectively, to operate the magnetic sensor in the reversed sensitivity during a second period of time.

8. The method of claim 6, further comprising determining an orientation of the subject based on the useful portion of the response signal.

9. A non-transitory computer readable medium that stores instructions executable by one or more processors to perform a method for surgical navigation, comprising:
measuring a first response signal received from at least one magnetoresistance sensor in response to a magnetic field when the magnetoresistance sensor has a reference sensitivity, wherein the magnetoresistance sensor is operatively coupled to a target device;
measuring a second response signal received from the magnetoresistance sensor in response to the magnetic field when the magnetoresistance sensor has a reversed sensitivity, wherein the reversed sensitivity is obtained by applying varying voltage configurations, frequency configurations, or a combination thereof to the magnetoresistance sensor while an alignment of one or more magnetic domains corresponding to the magnetoresistance sensor remains unchanged;
determining a useful portion of the first response signal of the magnetoresistance sensor by eliminating common-mode noise from the first response signal based on a difference between the first response signal and the second response signal; and
determining a position of the target device based on the useful portion of the first response signal.

* * * * *